US012778630B2

(12) United States Patent
Cynamon

(10) Patent No.: US 12,778,630 B2
(45) Date of Patent: Nov. 3, 2026

(54) METHOD FOR USING RAIL ANCHOR SYSTEM FOR TRANSJUGULAR INTRAHEPATIC PORTOSYSTEMIC SHUNT PROCEDURE

(71) Applicant: Jacob Cynamon, Suffern, NY (US)

(72) Inventor: Jacob Cynamon, Suffern, NY (US)

( * ) Notice: Subject to any disclaimer, the term of this patent is extended or adjusted under 35 U.S.C. 154(b) by 134 days.

(21) Appl. No.: 18/777,944

(22) Filed: Jul. 19, 2024

(65) Prior Publication Data

US 2024/0374286 A1 Nov. 14, 2024

Related U.S. Application Data

(62) Division of application No. 16/232,204, filed on Dec. 26, 2018, now abandoned.

(60) Provisional application No. 62/610,852, filed on Dec. 27, 2017.

(51) Int. Cl.
*A61B 17/34* (2006.01)
*A61B 17/00* (2006.01)

(52) U.S. Cl.
CPC ...... *A61B 17/3468* (2013.01); *A61B 17/3417* (2013.01); *A61B 2017/00292* (2013.01); *A61B 2017/3486* (2013.01); *A61B 2017/3488* (2013.01)

(58) Field of Classification Search
CPC ............ A61B 17/3468; A61B 17/3417; A61B 2017/00292; A61B 2017/3486; A61B 2017/3488; A61B 17/3403; A61B 17/34; A61M 2025/0681; A61M 2025/1047; A61M 25/0662; A61M 25/04; A61M 25/0606; A61M 25/10
USPC .......................................................... 606/108
See application file for complete search history.

(56) References Cited

U.S. PATENT DOCUMENTS

2004/0167606 A1* 8/2004 Chouinard ................ A61F 2/90 623/1.53
2015/0141836 A1* 5/2015 Naumann ............ A61B 8/0841 600/463
2015/0289929 A1* 10/2015 Toth ................... A61B 18/1492 606/41
2016/0015422 A1* 1/2016 De Cicco ............... A61B 17/11 600/464

* cited by examiner

*Primary Examiner* — Tan-Uyen T Ho
*Assistant Examiner* — Bridget E. Rabaglia
(74) *Attorney, Agent, or Firm* — David Colls; Berger Singerman LLP

(57) ABSTRACT

A rail and/or anchor system and method for transjugular intrahepatic portosystemic shunt procedures. The system includes a rail line that is anchorable to surrounding tissue and used as a rail to guide the displacement of at least one needle and an outer sheath. The rail line may include an inflatable balloon that is configured to selectively anchor the anchor line to surrounding tissue by the balloon being inflated and unanchor the anchor line to surrounding tissue by the balloon being deflated. The rail line is stiff. The rail line includes a lumen and is configured for executing wedge venography, and for measuring pressure at a tip of the rail line while a balloon of the balloon catheter is inflated. The anchor line may include one or more hooks for anchoring the anchor line to surrounding tissue. The one or more hooks may be selectively advanceable and retractable.

16 Claims, 10 Drawing Sheets

METHOD FOR USING RAIL ANCHOR SYSTEM FOR TRANSJUGULAR INTRAHEPATIC PORTOSYSTEMIC SHUNT PROCEDURE

CROSS-REFERENCE TO RELATED APPLICATION

This application claims the benefit of co-pending U.S. patent application Ser. No. 16/232,204 filed Dec. 26, 2018, and U.S. Provisional Patent Application Ser. No. 62/610,852 filed Dec. 27, 2017, which is incorporated herein in its entirety.

FIELD OF THE INVENTION

The present disclosure is generally directed to medical procedures, and more importantly to an improved Transjugular Intrahepatic Portosystemic Shunt (TIPS) procedure and system.

BACKGROUND OF THE INVENTION

A Transjugular Intrahepatic Portosystemic Shunt (TIPS) procedure includes connecting the portal vein (PV) to the hepatic vein (HV) in the liver. The purpose of the procedure is to divert blood from entering the liver, and may be executed on patients with cirrhosis and internal bleeding and/or ascites.

The most difficult portion of a TIPS procedure is accessing the portal vein from the hepatic vein. The device that is currently available requires significant expertise, and typically requires a 10 French sheath to be placed into the hepatic vein. A significant problem is that the 10 French sheath that is placed in to the hepatic vein often falls out of the hepatic vein and accessing the hepatic vein needs to be repeated. Also, aiming at the portal vein is usually performed blindly and aiming at and entering the portal vein can be difficult.

Existing TIPS devices are over 25 years old and do not have any provision for maintaining access in the hepatic vein or for performing repeat hepatic portal venography while attempting to create TIPS via the same 10 French sheath that has been initially inserted into the hepatic vein during the procedure.

Therefore, there exists a need for a system and method to maintain access to the hepatic vein and also a system and method for allowing repeated portal venography.

SUMMARY OF THE INVENTION

This summary is provided to introduce a selection of concepts in a simplified form that are further described below in the detailed description. This summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

As one example, disclosed is a rail and/or anchor system for transjugular intrahepatic portosystemic shunt procedures, the system comprising:

- a rail and/or anchor line or stiff shaft configured for being anchored to surrounding tissue and/or stiff enough configured to guide the displacement of at least one of a needle and an outer sheath.

In another aspect, the rail and/or anchor line is a balloon catheter, and a balloon of the anchor line is configured to selectively anchor the anchor line to surrounding tissue by the balloon being inflated, and unanchor the anchor line to surrounding tissue by the balloon being deflated. If a shaft of the catheter is stiff or stiffened by a wire, it can be used as a rail with the balloon inflated or deflated.

In another aspect, the rail and/or anchor line is a balloon catheter configured for executing wedge venography by discharging a gas or contrast through the balloon catheter while a balloon of the balloon catheter is inflated.

In another aspect, the rail and/or anchor line is a balloon catheter configured for measuring pressure at a tip of the balloon catheter while the balloon is inflated.

In another aspect, the rail and/or anchor line includes one or more hooks for anchoring the anchor line to surrounding tissue.

In another aspect, the rail and/or anchor line includes one or more hooks for anchoring the anchor line to surrounding tissue, and the one or more hooks are selectively advanceable and retractable.

In another aspect, the rail and/or anchor line includes a balloon and one or more hooks to anchor the anchor line to surrounding tissue.

As another example, disclosed is a rail and/or anchor system for transjugular intrahepatic portosystemic shunt procedures, the system comprising:

- an inner rail;
- an outer sheath configured to be advanced and retracted over the inner rail;
- a needle configured to be advanced between the inner rail and the outer sheath; and
- the inner rail with or without an anchor, the anchor configured to anchor the inner rail to surrounding tissue.

In another aspect, the inner rail includes a balloon catheter, and the anchor is a balloon of the balloon catheter, and the balloon is configured to anchor the inner rail to the surrounding tissue by being inflated and unanchor the inner rail to the surrounding tissue by being deflated.

In another aspect, the inner rail includes a balloon catheter for executing wedge venography by discharging a gas or contrast through the balloon catheter while a balloon of the balloon catheter is inflated.

In another aspect, the inner rail includes a balloon catheter for measuring pressure at a tip of the balloon catheter while the balloon is inflated.

In another aspect, the anchor includes one or more hooks to hook onto surrounding tissue.

In another aspect, the anchor includes one or more hooks to hook onto surrounding tissue, the one or more hooks being selectively advanceable and retractable.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

FIG. I schematically presents an exemplary method of performing a transjugular intrahepatic portosystemic shunt procedure, in accordance with aspects of the present disclosure.

Like reference numerals refer to like parts throughout the several views of the drawings.

DETAILED DESCRIPTION

Figure 2:
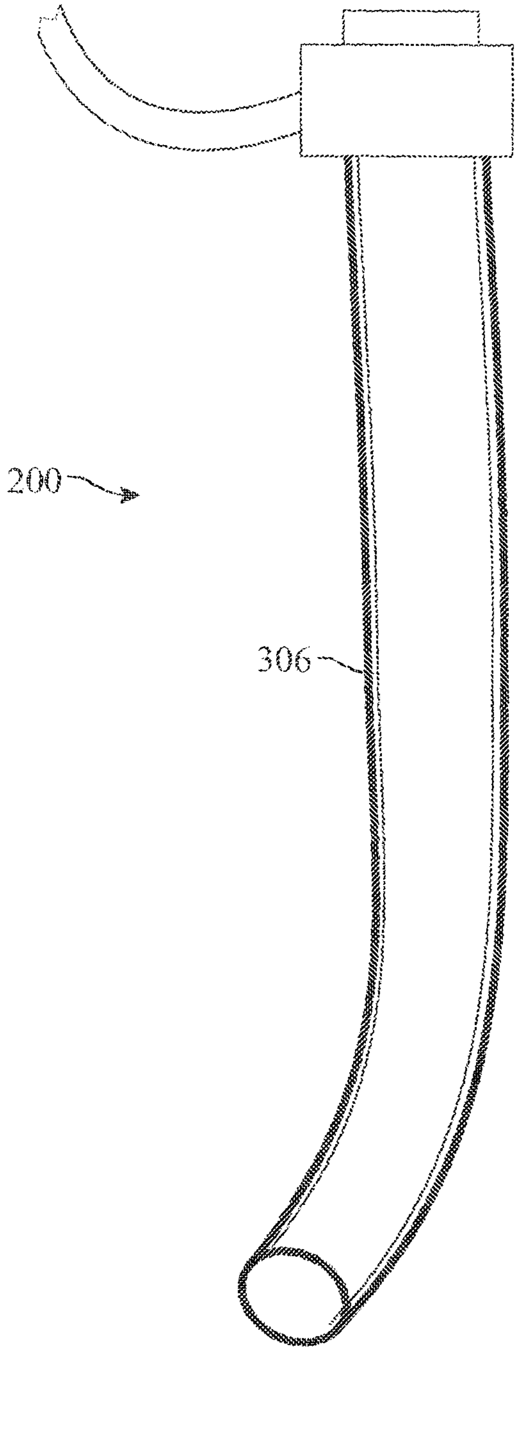
FIG. 2 schematically presents an outer sheath, in accordance with aspects of the present disclosure.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 2. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 3:
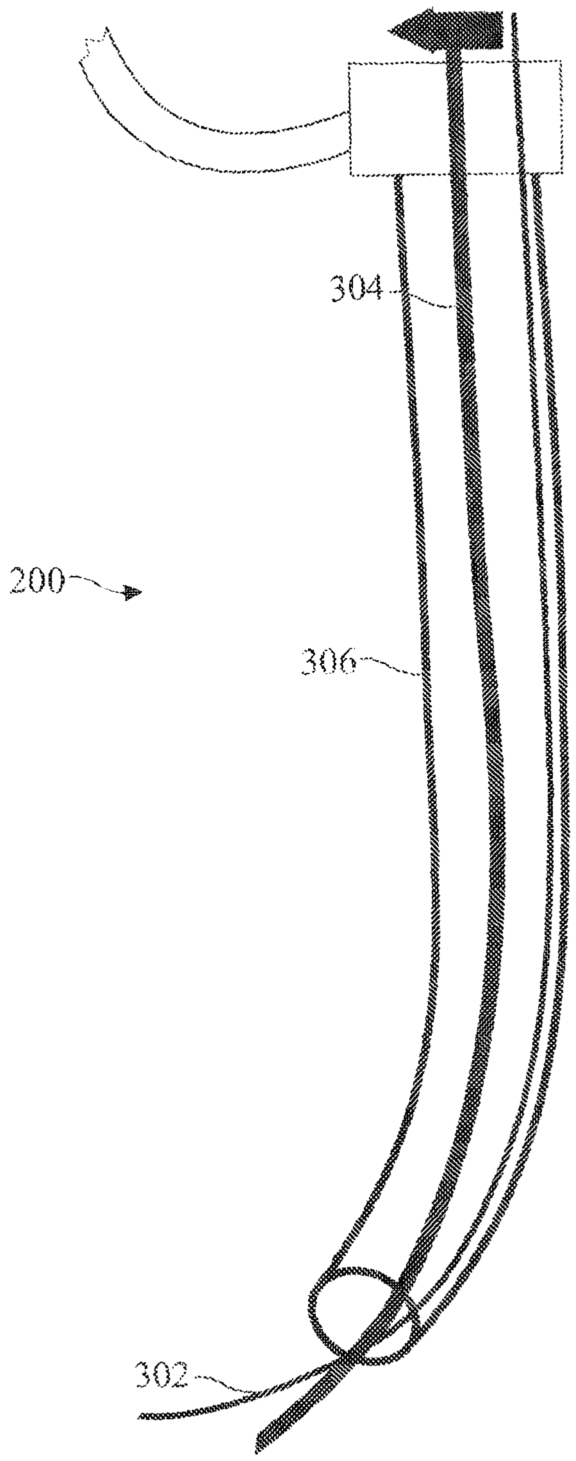
FIG. 3 schematically presents an outer sheath receiving an anchor line, rail, and/or stiff shaft catheter, and a needle, in accordance with aspects of the present disclosure.

Disclosed herein is a rail and/or anchor system 200 (FIGS. 2-10) and method 100 (FIG. 1) for transjugular intrahepatic portosystemic shunt procedures. As shown in FIG. 3, system 200 may include a rail and/or anchor line 302 configured for being anchored or secured (held in place) by its stiff shaft to surrounding tissue and configured to guide the displacement of at least one of a needle 304 and an outer sheath 306 (e.g a needle 304 and/or an outer sheath 306). For example, the anchor line 302 may allow the sheath to pass through itself, or outside itself in between an outer wall of the anchor line 302 and an outer sheath 306.

Figure 4:
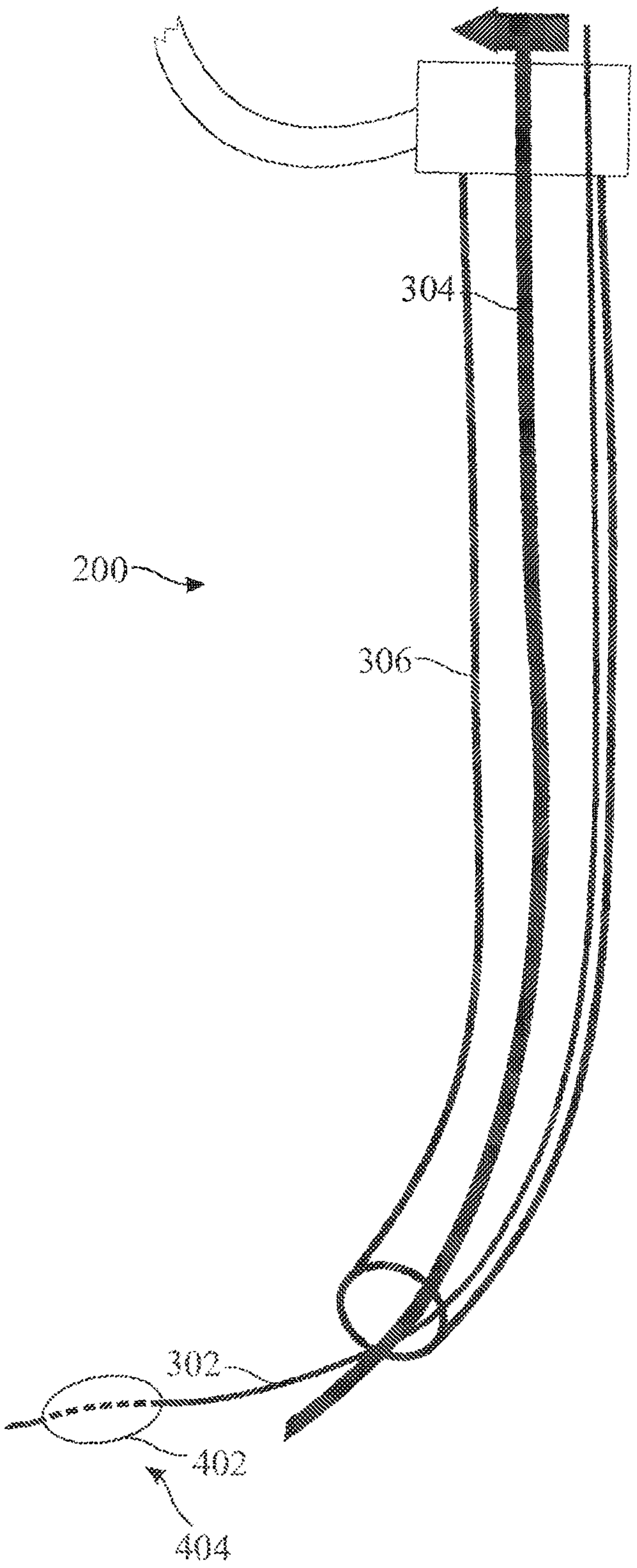
FIG. 4 schematically presents a balloon having been inflated, in accordance with aspects of the present disclosure.
Figure 5:
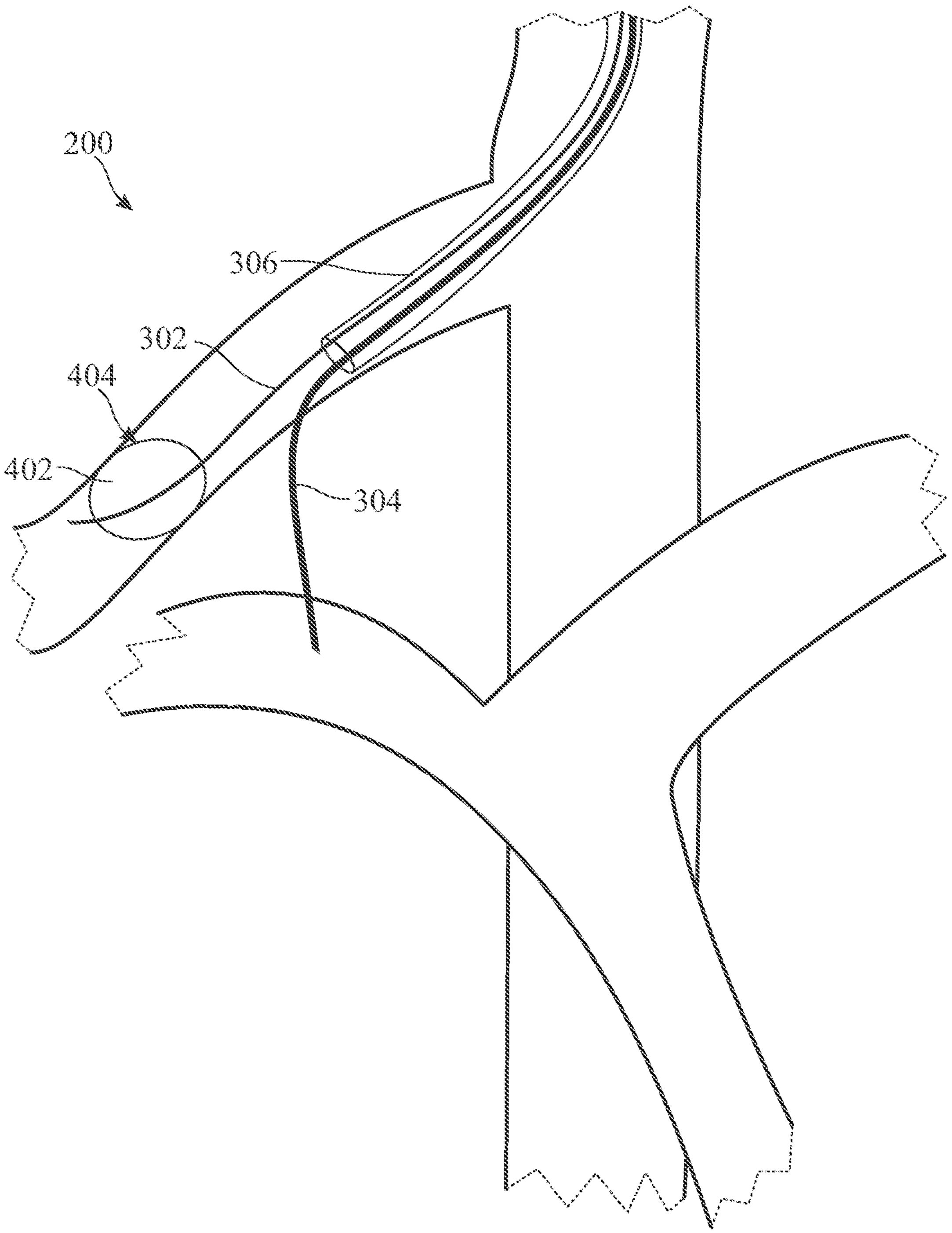
FIG. 5 schematically presents an exemplary use of the disclosed system, where a balloon has been inflated and a needle is puncturing nearby tissue, in accordance with aspects of the present disclosure.
Figure 6:
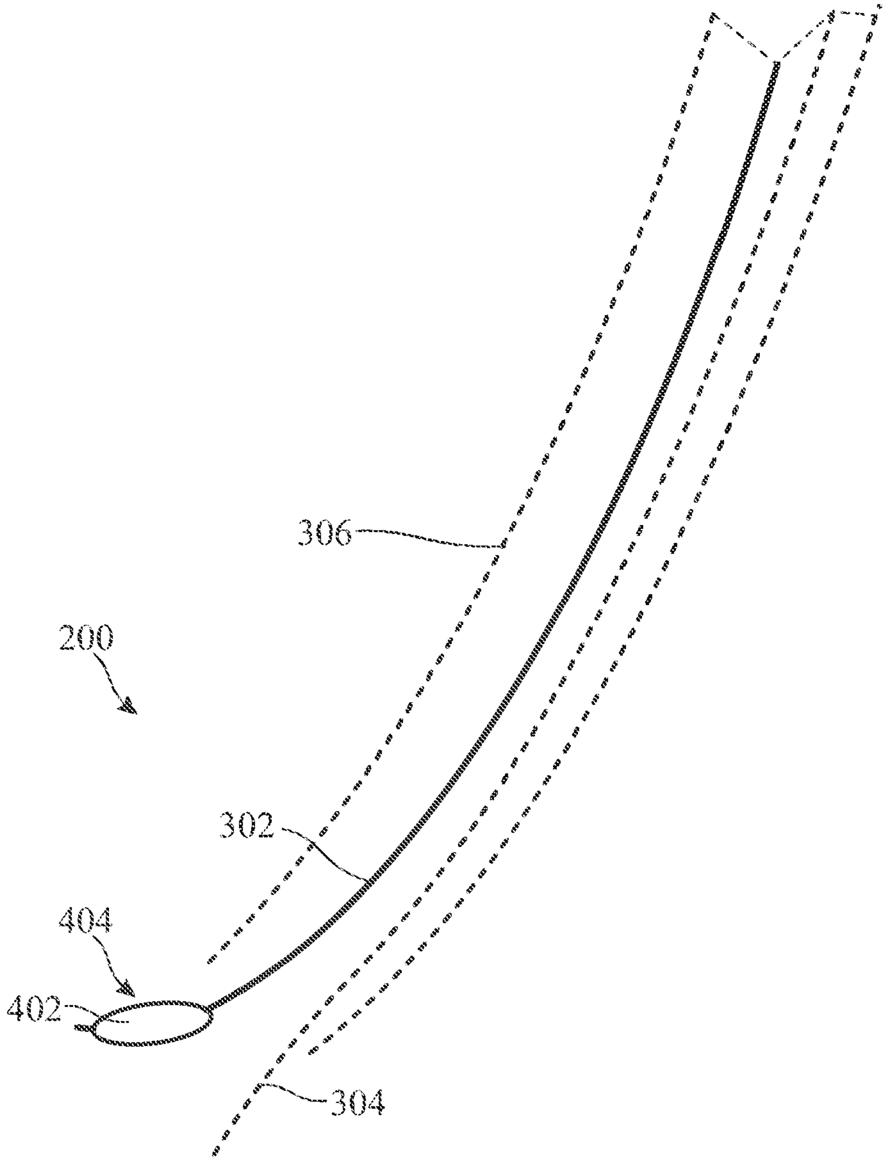
FIG. 6 schematically presents the anchor line with no hooks or retracted one or more hooks, and a deflated balloon, in accordance with aspects of the present disclosure.

In one example, turning to FIG. 4, the anchor line 302 is, or includes, a balloon catheter. A balloon 402 of the balloon catheter may be configured to selectively anchor the anchor line 302 to surrounding tissue by the balloon 402 being inflated (FIG. 5). The balloon may unanchor the anchor line 302 to surrounding tissue by the balloon 402 being deflated (FIG. 6). The balloon catheter may be configured for executing wedge venography by discharging a gas or contrast through the balloon catheter while a balloon 402 of the balloon catheter is inflated (FIG. 5). The balloon catheter may be configured for measuring pressure at a tip of the balloon catheter while the balloon 402 is inflated or deflated. The balloon catheter may be configured to function as a rail without an anchor if it is stiff shafted by means of wall stiffness or stiff wire.

Figure 7:
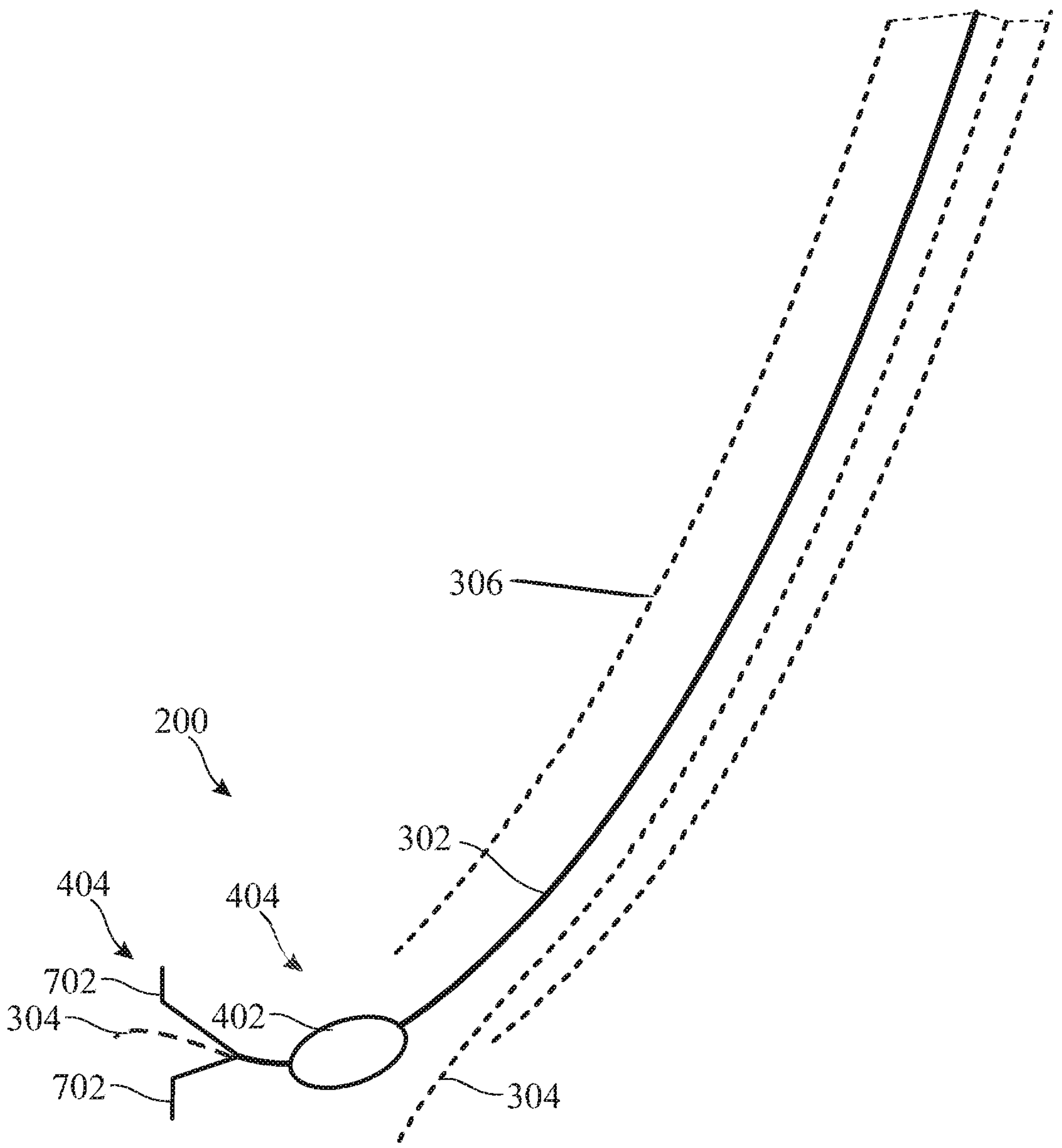
FIG. 7 schematically presents the rail and/or anchor line with extended two hooks, and an inflated balloon, in accordance with aspects of the present disclosure.
Figure 8:
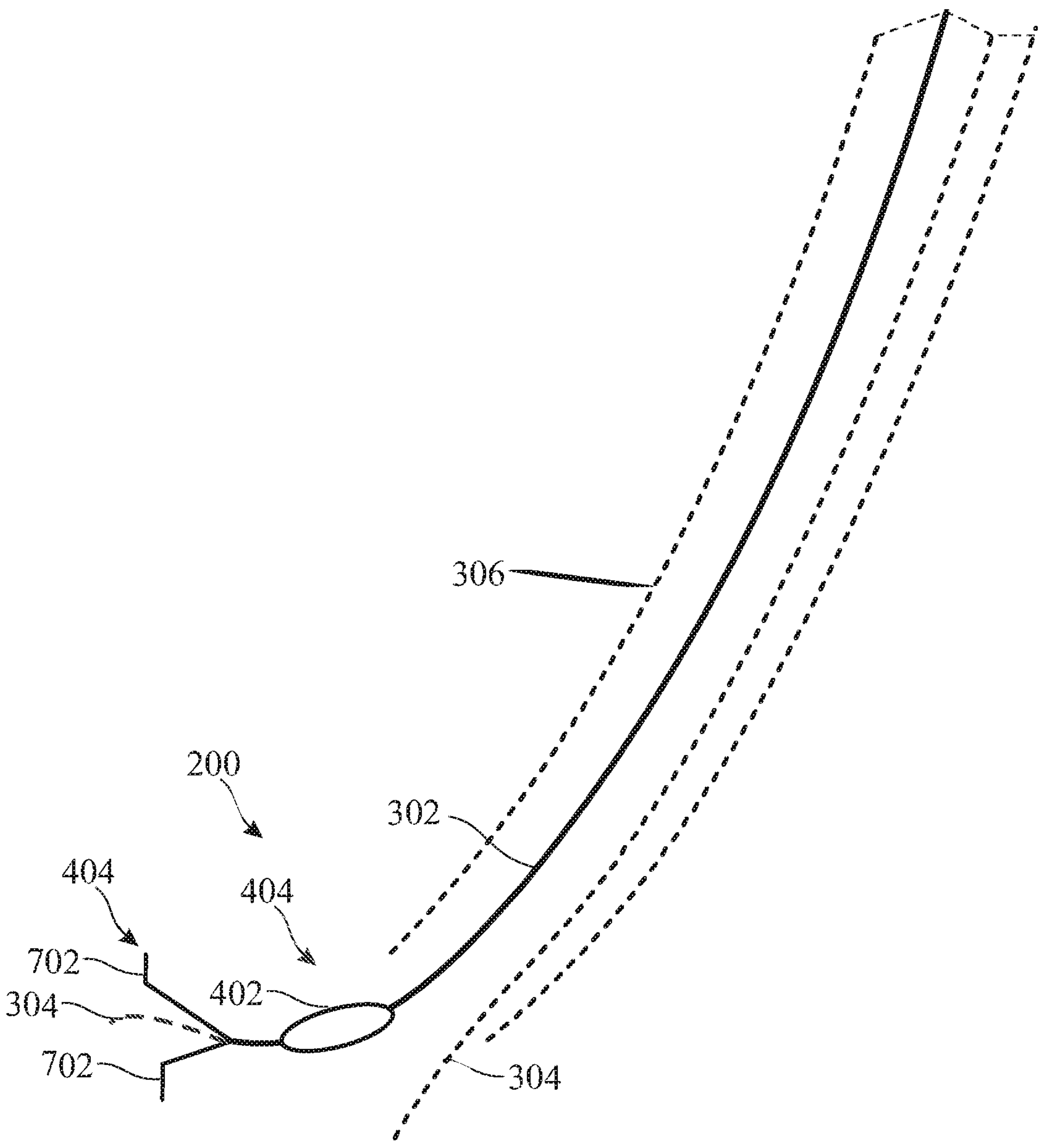
FIG. 8 schematically presents the anchor line with extended two hooks, and a deflated balloon, in accordance with aspects of the present disclosure.
Figure 9:
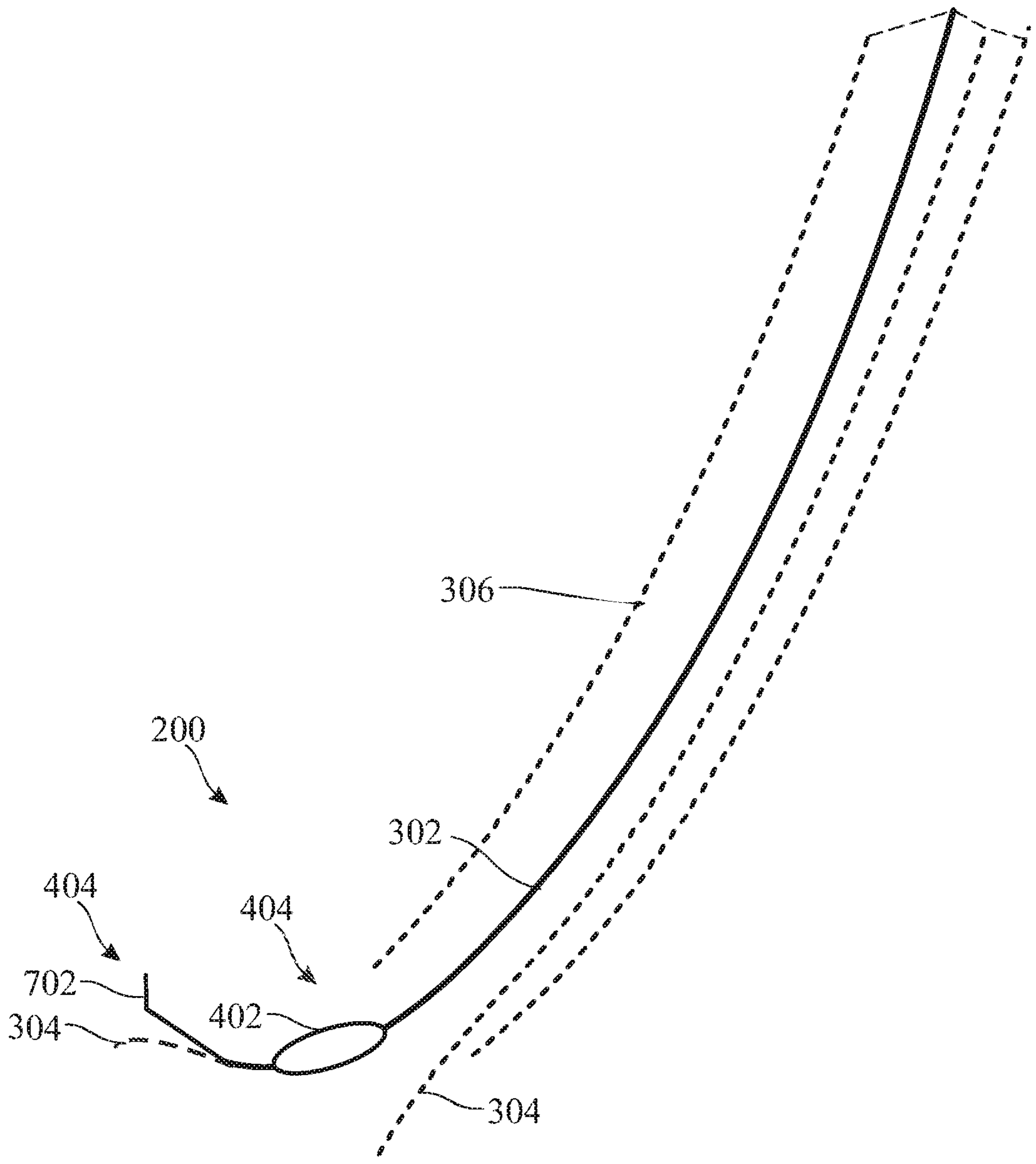
FIG. 9 schematically presents the anchor line with one extended hook, and a deflated balloon, in accordance with aspects of the present disclosure.
Figure 10:
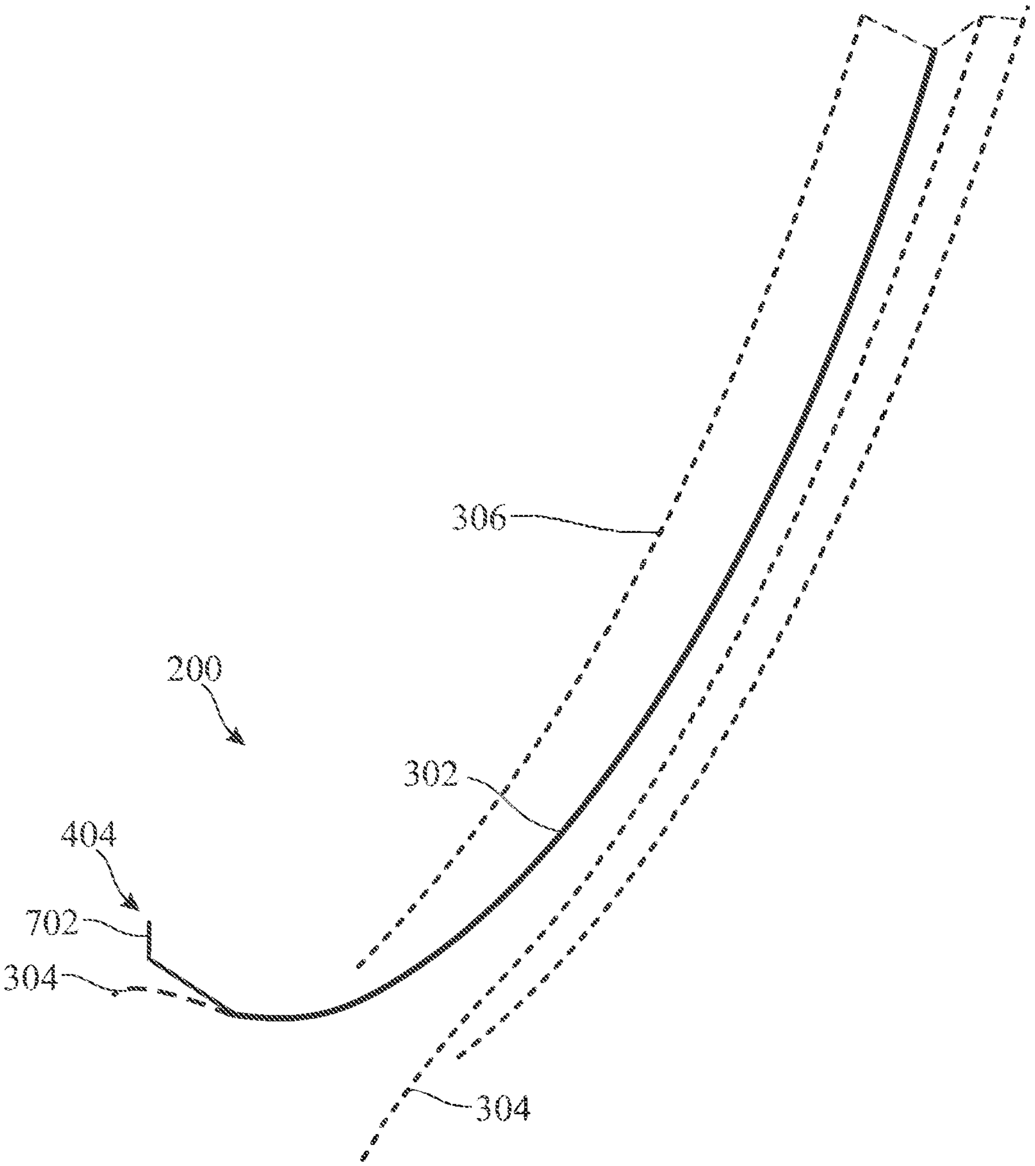
FIG. 10 schematically presents an anchor line having a single hook, without a balloon, in accordance with aspects of the present disclosure.

The anchor line 302 may include one or more hooks 702 (FIG. 7) for anchoring the anchor line 302 to surrounding tissue. The one or more hooks 702 may be selectively advanceable and retractable (FIGS. 6 and 7). The anchor line 302 may include a balloon 402 and one or more hooks 702 together, to anchor the anchor line 302 to surrounding tissue.

As another example, the system 200 includes an inner rail 302 and an outer sheath 306 configured to be advanced and retracted over the inner rail 302. The inner rail may include none or one or more features and elements of the anchor line 302 described above. The outer sheath 306 may be a 10 Fr sheath, for example. But any appropriate sheath may be included for enabling the features of the present disclosure. The system may include a needle 304 configured to be advanced between the inner rail 302 and the outer sheath 306. The inner rail 302 may include an anchor 404. The anchor 404 may be configured to anchor the inner rail 302 to surrounding tissue.

The inner rail 302 may include a balloon catheter, and the anchor 404 may be a balloon 402 (FIG. 4) of the balloon catheter. The balloon 402 may be configured to anchor the inner rail 302 to the surrounding tissue by being inflated. The balloon 402 may be configured to unanchor the inner rail 302 to the surrounding tissue by being deflated.

The inner rail 302 may include a balloon catheter for executing wedge venography by discharging a gas or contrast through the balloon catheter while a balloon 402 of the balloon catheter is inflated. The inner rail 302 may include a balloon catheter for measuring pressure at a tip of the balloon catheter while the balloon 402 is inflated.

The anchor 404 may include one or more hooks 702 (FIG. 7) to hook onto surrounding tissue. The one or more hooks 702 may be selectively advanceable and retractable. The anchor 404 may include a balloon 402 and one or more hooks 702, together, to anchor the inner rail 302 to surrounding tissue.

Further disclosed is a method 100 of performing a transjugular intrahepatic portosystemic shunt procedure. The method 100 may generally include advancing a rail and/or anchor line 302 into a patient, anchoring the anchor line 302 to surrounding tissue or using the rail positioned in the hepatic vain, and guiding the displacement of at least one of a needle 304 and an outer sheath 306 via the anchor line 302.

Figure 1:
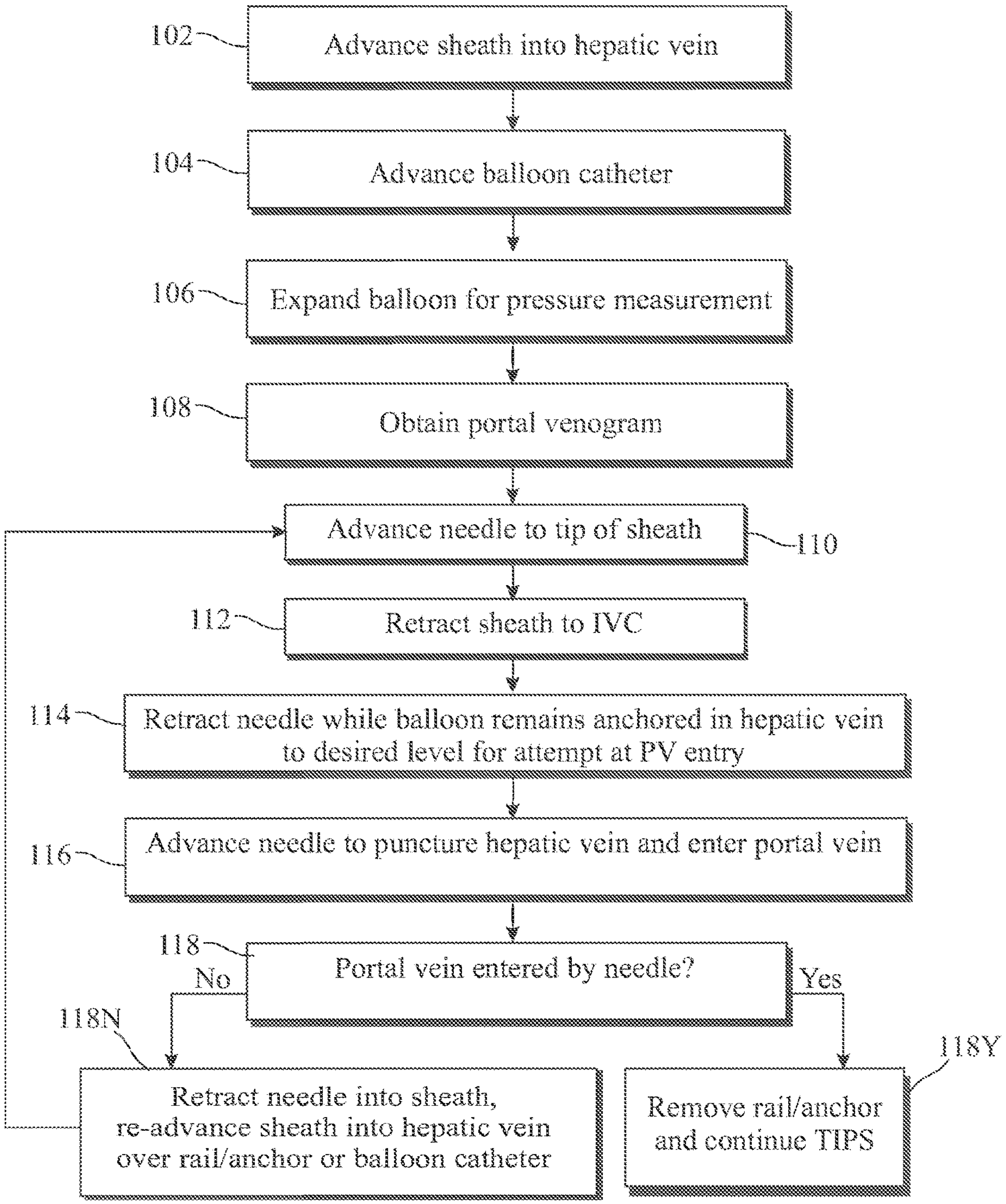

More particularly, with reference to FIG. 1, the method may include: at 102, advancing a sheath into a hepatic vein, at 104 advancing a balloon catheter through the sheath, at 106 expanding the balloon for pressure measurement, at 108 obtaining a portal venogram, at 110 advancing a needle to a tip of the sheath (either within the balloon catheter or between the balloon catheter and the sheath), at 112 retracting the sheath to the IVC, at 114 retracting the needle and/or the sheath while balloon remains anchored or positioned in hepatic vein to a desired level for attempt at PV entry, at 116 advancing the needle to puncture the hepatic vein and enter the portal vein, at 118 determining if the portal vein has been entered by the needle, at 118N if the portal vein is not entered by the needle retracting the needle into the sheath and readvancing the sheath into the hepatic vein over the balloon catheter, rail, and/or anchor, at 118Y ending the method if the portal vein has been entered by the needle, the balloon catheter, anchor, and/or rail is removed, the TIPS procedure then proceeds as usual. Step 118 and 118N may be repeated until the needle has entered the portal vein. After 118N, the method goes back to step 110 and is repeated.

In another example, the method includes removing a dilator after the sheath is advanced into the hepatic vein. Next, the balloon catheter may be advanced to a tip of the sheath. Next, free hepatic vein pressure may be measured, and next the balloon may be expanded to measure wedge pressure. Next, portal venography may be executed. For example, wedge portal venography may be performed while the needle is in the liver parenchyma to determine the position of the needle's tip in relation to the portal vein, Next, the a needle may be advanced to the tip of the sheath. Next, the sheath may be retracted while the balloon catheter and the needle remain in place. Next the needle may be retracted while the balloon remains anchored (or positioned) in the hepatic vein. When the needle is advanced to a desired point in the hepatic vein, the needle may be advanced to puncture the hepatic vein with the aim of entering the liver parenchyma and the portal vein. Next, if the portal vein was entered by the needle, the balloon catheter and/or anchor may be removed and the TIPS procedure may be subsequently completed.

If the portal vein is not entered by the needle, the needle may be retracted into the sheath, and the sheath may be re-advanced into the hepatic vein over the balloon catheter, anchor, and/or rail, and the needle may be re-advanced to the tip of the sheath. Next, the sheath may be retracted and the above described wedge portal venography and subsequent steps may be re-performed or re-attempted until the needle enters the liver parenchyma and portal vein.

In the method 100, the rail and/or anchor line 302 may be a balloon catheter, and a balloon 402 of the balloon catheter may be configured to selectively anchor the anchor line 302 to surrounding tissue by the balloon 402 being inflated, and unanchor the anchor line 302 by the balloon 402 being deflated. The method 100 may further include inflating the balloon 402 to anchor the anchor line 302. Alternatively, the rail and/or anchor line 302 can be used as a rail without anchoring if the catheter is positioned and maintained in the hepatic vein and the catheter was stiff or stiffened by a stiff wire.

In the method 100, the anchor line 302 may be a balloon catheter configured for executing wedge venography by discharging a gas or contrast through the balloon catheter while a balloon 402 of the balloon catheter is inflated. The method may further include executing wedge venography via the balloon catheter.

In the method 100, the anchor line 302 may be a balloon catheter configured for measuring pressure at a tip of the balloon catheter while the balloon 402 is inflated. The method 100 may further include measuring pressure at the tip of the balloon catheter while the balloon 402 is inflated.

In the method 100, the anchor line 302 may include one or more hooks 702 for anchoring the anchor line 302 to surrounding tissue. The method 100 may further include anchoring the anchor line 302 via the one or more hooks 702.

In the method 100, the anchor line 302 may include a balloon 402 and one or more hooks 702, together, to anchor the anchor line 302 to surrounding tissue. The method may further include anchoring the anchor line 302 via at least one of the balloon 402 and the one or more hooks 702.

In other words, the disclosed TIPS system and method primarily maintains access in the hepatic vein and also limits the need for multiple passes through the parenchyma of the liver. For example, a stiff wire (inner rail 302 or anchor line 302) in a sheath (outer sheath 306) may maintain access of the hepatic vein while attempts at entering the portal vein can be made anywhere along the hepatic vein (even at the hepatic vein IVC junction without falling out of the hepatic vein). Maintaining access of the hepatic vein without the fear of the sheath falling out would allow the operator to puncture the hepatic vein close to the IVC which may be a preferred location for the puncture.

The method 100 may include using an occlusion balloon type catheter (including balloon 402) through the sheath to act as an anchor (e.g. anchor 404) and also allows one to perform repeated balloon occlusion venography to allow the operator to target a visualized portal vein (i.e. visualized via the venography). A balloon occlusion gives the advantages of allowing a proximal hepatic vein puncture and an added advantage of being able to perform repeated wedge portal venography.

As a non-limiting example, the disclosed system may be provided as a kit, including a stiff guidewire, Robust 10 Fr Sheath, a TIPS needle, and an occlusion balloon, or any appropriate element described herein. The stiff guidewire (inner rail 302 or anchor line 302) maintains access in the hepatic vein. The 10 Fr sheath is advanceable over the guidewire into the hepatic vein. An occlusion balloon may be inserted through the sheath over the guidewire or directly and the guidewire may be removed. It is to be understood that removing the guidewire may be optional, and the guidewire may or may not include the herein disclosed hook anchors. The needle may be advanced through the sheath into the hepatic vein. The sheath may be withdrawn over the guidewire, catheter, and/or rail to expose the needle. The needle may be retracted to the desired location in the hepatic vein and exit the hepatic vein and enter the liver parenchyma anywhere along the hepatic vein without fear of losing access due to the disclosed innovation of anchoring the inner rail 302 or anchor line 302 or by means of a stiff shaft catheter (no anchors). The balloon catheter may be used for repeat wedged venography.

When a balloon is inflated and obstructs the flow in the hepatic vein, the pressure reading at the tip of the catheter will read the pressure in the portal vein, where this pressure may be referred to as wedge pressure. Wedge pressure may reflect a true portal pressure that is measured directly in the portal vein. One issue in the prior art is that repeat portal venography is not possible once entry into the portal vein is attempted. It may be important to know the pressure before an attempt is made to insert the needle into the portal vein. This pressure may be obtained by a pressure reading at a tip of the balloon catheter while the balloon is inflated. The wedge pressure may be determined while the balloon is inflated, because the balloon obstructs outflow through the hepatic vein, and the portal venous pressure is transmitted through the liver parenchyma to the tip of the balloon catheter.

Therefore, the balloon catheter may be used for at least two functions during the TIPS procedure. One function of the balloon catheter is to execute repeat portal venograms at any point during the procedure and a second function is to maintain access of the hepatic vein so that the TIPS sheath used to access the hepatic vein does not fall out of the hepatic vein and the sheath can be pulled back into the IVC or right atrium and then re-advanced back into the hepatic vein over the balloon catheter if needed. A stiffened balloon catheter may be used to add both stiffness to the device during insertion and to effect repeated portal venograms and to advance the sheath over it as a rail even if the sheath is retracted into the IVC or Right Atrium. In a wedge portal venogram, the balloon may be inflated and contrast or carbon dioxide gas may be injected to show the portal vein.

The carbon dioxide gas may be any appropriate gas, without departing from the scope of this disclosure. The carbon dioxide gas is discharged distally with respect to the balloon and its respective catheter (e.g. the gas may be discharged from a tip of the balloon catheter). In some examples, the carbon dioxide gas may be injected through the outer sheath (e.g. 10 fr sheath), external to the balloon catheter. In yet another example, carbon dioxide gas may be proximally located with respect to an inflated balloon, without departing from the scope of the present disclosure. It is to be understood that the term proximal refers to a general area or direction away from a working tip of the device, and distal refers to a general area of direction toward a working tip of the device.

In one example, the required stiffness of the device (e.g. for advancing the sheath into the hepatic vein) may be provided solely, or majorly, by a selected material of the IO Fr sheath, or by a selected material of the balloon catheter, or by a selected material of guide wire, or a combination thereof. The stiffness of the device is to be adjusted, selected, or configured to prevent herniation during inserting the device or advancement of the sheath over the catheter.

This new system simplifies the TIPS procedure. The guidewire or occlusion balloon will maintain hepatic vein access. The needle will be able to be advanced (e.g. bareback) through the IO Fr sheath without kinking or piercing the sheath. In some examples, the needle may need to be protected by a IO Fr dilator to advance it safely through the IO Fr sheath. The IO Fr sheath may need to be strengthened so as to allow the needle (e.g. needle 304) to be advanced bareback. A wire and/or balloon will be specific for this application so that the wire/balloon would fit the IO Fr sheath. In addition an appropriate balloon catheter to dilate the liver parenchyma and a covered stent may be required to complete the TIPS procedure.

It is anticipated that various other configurations may anchor the catheter, sheath, or generally the device, in the hepatic vein to thereby implement a rail for the sheath to move up and down the rail. The balloon catheter can be used as an anchor, a catheter (without a balloon) can be used as an anchor, or just a wire with an anchor element, such as a hook, can be used as an anchor. In another example, a wire that is stiff enough can be used as an anchor. It is to be understood that the term "hook" may refer to any appropriate structure that selectively (or temporarily) attaches to tissue, and it may be a J-shaped or L-shaped structure having a pointed or sharp distal end.

A balloon catheter may have an inflatable and deflatable balloon. Anchor elements such as hooks or spokes, similar to spokes or ribs of an umbrella, may be selectively deployed from the catheter to anchor into hepatic tissue and can be selectively released from the hepatic tissue to remove the catheter. The anchor may be a balloon, and/or have one or more hooks. In one example, the balloon may be eliminated from the anchor, such that a wire has an anchor mechanism without a balloon. The hook anchor may be retractable within its respective catheter.

It is to be understood that reference to a balloon catheter and/or a guide wire may refer to the above referenced anchor line 302 and/or inner rail 302. Therefore, a needle may pass through the balloon catheter, or through a sheath that holds a wire having one or more hooks. The needle may also pass along an outer portion of the balloon catheter between the balloon catheter and an outer sheath (e.g. IO fr sheath). In one example, the device includes a balloon catheter and a needle passing within the balloon catheter, or through a hole in a wall of the balloon catheter.

It is anticipated that, without departing from the scope of this disclosure, that a stiff shaft balloon catheter/sheath may have a side hole allowing for needle exit from the catheter/sheath. Such an aperture may be approximately 4 cm from the distal end of the catheter/sheath. The needle may exit the hole either by advancing the needle from a hub (proximal) end all the way out, or the needle may be built into the catheter/sheath and advanced out into the liver. The end 4 cm will anchor the catheter/sheath and be used for contrast or carbon dioxide portography.

In conclusion, the disclosed system allows a simpler method of performing a TIPS procedure by anchoring a guide device and/or rail that guides and positions a needle and/or an outer sheath.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method of performing a transjugular intrahepatic portosystemic shunt procedure, comprising the steps of:
- providing a medical device, comprising,
  - a stiff rail line including an inflatable balloon positioned proximal to a terminal distal end of the stiff rail line;
- providing a sheath with a singular lumen;
- providing at least one TIPS needle;
- advancing and positioning the stiff rail line within a targeted area surrounding hepatic vein tissue;
- advancing the sheath over the stiff rail line; and
- advancing the TIPS needle within the singular lumen of the sheath alongside the stiff rail line toward the hepatic vein tissue;
- retracting the sheath over the stiff rail line while the balloon remains anchored within the targeted area surrounding the hepatic vein tissue,
  - wherein the stiffness of the stiff rail line is configured to allow the advancement and retraction of the outer sheath over the stiff rail line,
  - wherein the stiffness of the stiff rail line is configured to allow the TIPS needle to advance through the sheath bareback without kinking or piercing the sheath toward the targeted area,
  - wherein the stiffness of the stiff rail line is configured to allow a distal end of the TIPS needle to extend beyond a distal end of the sheath to expose the distal end portion of the TIPS needle to the surrounding hepatic vein tissue for piercing, and wherein the balloon is configured to selectively anchor the stiff rail line to the targeted area by the balloon being inflated outside of the sheath, and unanchor the stiff rail line to the targeted area by the balloon being deflated.

2. The method of claim 1, wherein a wedge venogram is possible when the balloon is inflated within the targeted area surrounding the hepatic vein tissue.

3. The method of claim 1, wherein portal venography is possible when the balloon is inflated within the targeted area surrounding the hepatic vein tissue.

4. The method of claim 1, wherein the stiff rail line includes one or more hooks at a distal end of for alternatively anchoring the stiff rail line to the targeted area surrounding the hepatic vein tissue.

5. The method of claim 1, wherein a dilator is advanceable over the stiff rail line.

6. The method of claim 1, wherein the stiff rail line includes a lumen and at least one aperture and that intersects with the lumen.

7. The method of claim 6, wherein the at least one aperture is sufficiently sized to allow passage of the TIPS needle therethrough.

8. The method of claim 6, wherein the at least one aperture is approximately 4 cm from the terminal distal end of the stiff rail line.

9. The method of claim 6, wherein the at least one aperture is provided superior to the balloon on the stiff rail line.

10. A method of performing a transjugular intrahepatic portosystemic shunt procedure, comprising the steps of:

providing a medical device, comprising, a stiff rail line including an inflatable balloon positioned proximal to a terminal distal end of the stiff rail line;

providing a sheath with a singular lumen;

providing at least one TIPS needle;

advancing and positioning the stiff rail line within a targeted area surrounding hepatic vein tissue;

inflating the balloon at the targeted area;

advancing the sheath over the stiff rail line;

advancing the TIPS needle within the singular lumen of the sheath alongside the stiff rail line toward the hepatic vein tissue;

retracting the sheath over the stiff rail line while the balloon remains anchored within the targeted area surrounding the hepatic vein tissue; and puncturing the hepatic vein tissue and entering a targeted area within a portal vein;

wherein the stiffness of the stiff rail line is configured to allow the advancement and retraction of the outer sheath over the stiff rail line, wherein the stiffness of the stiff rail line is configured to allow the TIPS needle to advance through the sheath bareback without kinking or piercing the sheath, wherein the stiffness of the stiff rail line is configured to allow a distal end of the TIPS needle to extend beyond a distal end of the sheath to expose the distal end portion of the TIPS needle to the surrounding hepatic vein tissue for piercing, and wherein the balloon is configured to selectively anchor the stiff rail line to the surrounding hepatic vein tissue by the balloon being inflated outside of the sheath, and unanchor the stiff rail line to the surrounding hepatic vein tissue by the balloon being deflated.

11. The method of claim 10, wherein a wedge venogram is possible when the balloon is inflated within the targeted area surrounding the hepatic vein tissue.

12. The method of claim 10, wherein a dilator is advanceable over the stiff rail line.

13. The method of claim 10, wherein the stiff rail line includes one or more hooks at a distal end of for alternatively anchoring the stiff rail line to the targeted area surrounding the hepatic vein tissue.

14. The method of claim 10, wherein portal venography is possible when the balloon is inflated within the targeted area surrounding the hepatic vein tissue.

15. The method of claim 10, wherein repeated portal venographies are possible when the balloon is inflated within the targeted area surrounding the hepatic vein tissue.

16. A method of performing a transjugular intrahepatic portosystemic shunt procedure, comprising the steps of:

providing a medical device, comprising, a stiff rail line including an inflatable balloon positioned proximal to a terminal distal end of the rail line;

providing a sheath with a singular lumen;

providing at least one TIPS needle;

advancing and positioning the stiff rail line within a targeted area surrounding hepatic vein tissue;

inflating the balloon at the targeted area;

advancing the sheath over the stiff rail line;

advancing the TIPS needle within the singular lumen of the sheath alongside the stiff rail line toward the hepatic vein tissue;

retracting the sheath over the stiff rail line while the balloon remains anchored within the targeted area surrounding the hepatic vein tissue; and puncturing the hepatic vein tissue and entering a targeted area within a portal vein;

wherein the stiffness of the stiff rail line is configured to allow the advancement and retraction of the outer sheath over the stiff rail line, wherein the stiffness of the stiff rail line is configured to allow the TIPS needle to advance through the sheath bareback without kinking or piercing the sheath, wherein the stiffness of the stiff rail line is configured to allow a distal end of the TIPS needle to extend beyond a distal end of the sheath to expose the distal end portion of the TIPS needle to the surrounding hepatic vein tissue for piercing, wherein the balloon is configured to selectively anchor the stiff rail line to the surrounding hepatic vein tissue by the balloon being inflated outside of the sheath, and unanchor the stiff rail line to the surrounding hepatic vein tissue by the balloon being deflated, wherein portal venography is possible when the balloon is inflated within the targeted area surrounding the hepatic vein tissue, and wherein a wedge venogram is possible when the balloon is inflated within the targeted area surrounding the hepatic vein tissue.

* * * * *